United States Patent [19]
Seiden et al.

[11] Patent Number: 5,604,297
[45] Date of Patent: Feb. 18, 1997

[54] DEGASSING TECHNIQUES APPLIED TO SEALED CONTAINERS FOR BEVERAGES, WASTE WATER AND RESPIROMETERS FOR BACTERIA

[76] Inventors: Louis W. Seiden, 11,100 Rosemont Dr., N. Bethesda, Md. 20852; Marc J. Epstein, 14 Beach Ave., Leonardo, N.J. 07737; Steven A. Seiden, 3701 Lail Ct., Raleigh, N.C. 27606

[21] Appl. No.: 431,088

[22] Filed: Apr. 28, 1995

Related U.S. Application Data

[63] Continuation-in-part of Ser. No. 48,641, Apr. 2, 1993, Pat. No. 5,426,593, which is a continuation-in-part of Ser. No. 656,713, Feb. 19, 1991, Pat. No. 5,220,513.

[51] Int. Cl.$^6$ .................................................. G01N 33/18
[52] U.S. Cl. ............................ 73/19.1; 422/68.1; 436/62
[58] Field of Search ........................... 73/19.01, 19.03, 73/19.1; 422/68.1, 79, 80; 436/62

[56] References Cited

U.S. PATENT DOCUMENTS

| | | | |
|---|---|---|---|
| 3,684,702 | 8/1972 | Hartmann | 422/79 |
| 3,731,522 | 5/1973 | Mikesell | 73/19.01 |
| 3,740,320 | 6/1973 | Arthur | 73/19.01 |
| 3,868,223 | 2/1975 | Robock et al. | 436/62 |
| 4,437,992 | 3/1984 | Saito et al. | 210/603 |

*Primary Examiner*—Hezron E. Williams
*Assistant Examiner*—Daniel S. Larkin

[57] ABSTRACT

The invention relates to devices and methods for ultrasonically degassing a sealed container of fluid such as a container of beer, wine or soda. The invention further relates to methods and apparatus for measuring the respiration rate of bacteria in a test liquid containing bacteria such as waste water or activated sludge. The invention also relates to methods for measuring one or more components of the gas released from the sealed container utilizing ultrasonic and other degassing techniques and to methods for expanding head space of the container.

6 Claims, 6 Drawing Sheets

DEGASSING TECHNIQUES APPLIED TO SEALED CONTAINERS FOR BEVERAGES, WASTE WATER AND RESPIROMETERS FOR BACTERIA

REFERENCE TO RELATED APPLICATIONS

This application is a continuation-in-part of U.S. patent application Ser. No. 08/048,641, filed Apr. 2, 1993, now U.S. Pat. No. 5,426,593, which is a continuation-in-part of U.S. patent application Ser. No. 07/656,713, filed Feb. 19, 1991, issued as U.S. Pat. No. 5,220,513.

BACKGROUND

1. Field of the Invention

This invention relates to methods and apparatus for the controlled degassing of closed and sealed containers of liquid such as beverages, waste water and activated sludge using precision ultrasonics, sparging or stirring. The invention also relates to methods and apparatus for controlling the amount of headspace in a container of liquid.

2. Description of the Background

Ultrasonics has been used in the beverage industry for many years as one of the techniques for degassing containers to measure the level of carbon dioxide ($CO_2$) or nitrogen ($N_2$) in beverages such as soft drinks, beer and carbonated alcoholic products. However, ultrasonics has had only limited acceptance as an accurate method for determining the level of gases in a beverage. For the most part, these gases are artificially introduced into the beverage as part of the production process although some trace amount may be present from the atmosphere. Ultrasonics agitation is also suitable for measuring small amounts of oxygen ($O_2$) that may unavoidably enter the beverage during the production process.

The degassing process, especially the rate of degassing, is dependent on the ultrasonic power density at the beverage. Standard ultrasonics, available to the beverage industry, have not been developed as precision instruments for degassing to determine gas content. This lack of precision limited the use of ultrasonics for determining the quantities of various beverage gasses ($CO_2$, $O_2$, $N_2$).

The problem in any ultrasonic technique, where repeatability is an issue, is to use a device where the power density at the drink is held constant at the beverage for any test at any time. Most electronic ultrasonic devices use resonance circuits tuned to a particular ultrasonic frequency in the 20K Hz to 50K Hz range. However, the strength of the resonance and hence the strength of the ultrasonic waves that are produced are affected by the loading from every element in the electro-mechanical configuration. This includes (i) the beverage container size, (ii) the material of the container and its contents, (iii) the water level in the ultrasonic tank, (iv) the impedance of the electronic circuit, (v) the geometry of the ultrasonic tank, (vi) the temperature and density of the liquid in the ultrasonic tank and beverage container, (vii) other mechanical parts inserted into the ultrasonic tank such as hangers and supports for the beverage container, and (viii) variations in AC line power.

SUMMARY OF THE INVENTION

The present invention overcomes the problems and disadvantages associated with current strategies and designs and provides methods and apparatus for degassing liquid containers.

One embodiment of the invention is directed to devices for measuring an amount of a gas in a sealed container of fluid. The device is comprised of a piercing mechanism for piercing the sealed container, a precision ultrasonic degassing mechanism connected to the piercing mechanism, one or more electronic control circuits to maintain an ultrasonic power independent of loading conditions, a test chamber which receives a sample of gas released from the pierced container and connected to at least one additional chamber selected from the group consisting of a foam chamber, an expansion chamber, a buffer chamber, an extra test chamber and a combination thereof, and a gas specific sensor connected to said test chamber to measure the amount of a component of the released gas in said sample.

Another embodiment of the invention is directed to methods for measuring an amount of a gas in a sealed container of fluid. A piercing mechanism pierces the sealed container which is degassed with a precision degassing mechanism connected to the piercing mechanism wherein one or more electronic control circuits maintain a nearly constant ultrasonic power which is independent of loading conditions. A sample of the released gas is received into a test chamber and passed through at least one additional chamber which may be a foam chamber, an expansion chamber, a buffer chamber, an extra test chamber and a combination thereof. An amount of a component of the released gas of the sample is measured in the test chamber with a gas specific sensor.

Another embodiment of the invention is directed to methods for expanding a head space in a sealed container of fluid. The sealed container is agitated to release a gas dissolved in the fluid to the head space wherein pressure within said head space increases and moves an expansion element in a direction. The expansion element is pushed in an opposite direction to transfer the released gas to a test chamber.

Another embodiment of the invention is directed to methods for measuring the respiration rate of bacteria. A degassing chamber is filled with a test liquid containing bacteria such as waste water or activated sludge. The chamber is degassed using, for example, sparging or stirring, and a sample of the released gas is passed into a test chamber. The respiration chamber contains the liquid and bacteria and the test chamber contains the sensors for measuring the released gases. An additional expansion chamber is useful for checking the calibration of the device with different volumes; an additional test chamber is useful for isolating sensors and an additional buffer chamber is useful for isolating or removing interfering gases or vapors. An amount of a component of the released gas of said sample is measured in the test chamber with a gas specific sensor and the respiration rate of bacteria of the liquid is determined.

Other embodiments and advantages of the invention are set forth, in part, in the description which follows and, in part, will be obvious from this description and may be learned from the practice of the invention.

DESCRIPTION OF THE INVENTION

As embodied and broadly described herein, the present invention is directed to apparatus and methods which are useful for overcoming problems associated with the use of ultrasonics as a degassing mechanism for beverages. These methods and apparatus are easily controlled, repeatable and precise, and can also be used for expanding and controlling the head space of a container of liquid such as a beverage container.

Sealed containers such as beverage containers are typically processed with a substantial amount of external gases (e.g. $CO_2$ and $N_2$) artificially introduced into the liquid or trace gasses such as oxygen ($O_2$). There are many techniques which are presently available for degassing these sealed containers. Conventional techniques have several short comings that may affect the precision of the degassing including unreliability of power generation and problems associated with the container or the liquid itself.

The present invention overcomes these problems by utilizing electronic control circuits to maintain a constant, effective and efficient control over the process. For example, the use of electronic circuits minimizes uncertainty due to unpredictable power generations by the ultrasonics transducer, a partially failed component that allows operation at different power levels, aging of a component, especially the ultrasonic transducer, loading of the electronics due to the beverage container size and beverage composition, water level in the ultrasonic tank, geometry of the ultrasonics tank, such as cylindrical, hangers and other parts inserted into the ultrasonics tank, and temperature variations and time used for degassing. The ultrasonics unit is also tunable over a considerable range and the power output of the transducer is monitored by a watt meter. The power density from ultrasonic generation at the beverage that is being degassed is maintained nearly constant.

Units may be designed and built specifically for use in the beverage industry. For example, when the precision ultrasonic is integrated into a gas measuring system that incorporates an expansion chamber which allows the head space of the beverage container to be effectively increased, the volume of the expanded head space can be effectively controlled. The expansion chamber receives some or all of the beverage from a pierced or opened container, that had been previously sealed before the gas released from the beverage is allowed to enter the gas test chamber.

According to the present invention, a precision ultrasonic technique can be used that allows for repeatable measurements of various gases, such as $CO_2$, $N_2$ and $O_2$, that most commonly appear in beverages. The three elements that can be blended to create a precision tabletop ultrasonic unit include control, monitoring and tunability. In addition, this device may also be incorporated into a proper piercing device to open the sealed container in order that it may be degassed.

A minimized tabletop configuration uses a cylindrical stainless steel container tank mounted inside of a second stainless steel cylinder which serves as a skin and mount for the tank. The diameter of the container is sufficient so that a three liter beverage container can fit into the ultrasonic tank with some clearance between the outer wall of the beverage container and the inner walls of the ultrasonic tank. One or two ultrasonic transducers, with one or more piezoelectric wafers on each transducer, are mounted on the flat bottom of the tank with sufficient extra area to allow proper electronic control and sufficient power generation which is held at least nearly constant and independent of a change in any loading factors. Ultrasonic power is manifested by the ultrasonic wave in the liquid which is generated by the piezoelectric wafer and interacts with the dissolved $CO_2$ causing expansion (explosion) of discontinuity sites, or bubbles, and degassing. The preferred configuration is a cylindrical ultrasonic tank about 7½ inches in diameter and 8 inches in height with a volume of 5 quarts. Other larger tabletop units would allow more than one beverage container to be agitated simultaneously. In this case, some other geometry may be preferred and several transducers may be necessary to maintain the ultrasonic agitation power at the beverage.

There are numerous designs for control circuits such as the RC circuit used in this invention to control power in a load that includes the ultrasonic transducer and the power supply driver and forms a resonance circuit. The RC circuit determines the time required to charge the capacitor C to a sufficient voltage for a diode type switch to turn on. This provides the gate signal for the controlled power device to turn on. Power delivered to the load in each cycle depends on the portion of each cycle required to charge the capacitor to the firing potential of the diode type switch. The power to the load is changed by varying the resistor R or capacitor C in the timing circuit. The circuit current is essentially determined by the load resistance.

The power/timing cycle can be varied with a precision potentiometer which changes the timing cycle by varying the resistance in the RC circuit and alters the level of the constant ultrasonic power to the value required. This power level is maintained and monitored by a watt meter incorporated into the circuit. The watt meter properly represents the power of the ultrasonic waves by measuring the peak voltage (Vp), the peak current (Ip), and the phase angle (cosA) according to the formula: Power=½VpIp(cosA)

In this manner, with proper feedback, the ultrasonic power can be maintained at any level that is in the range of the control circuit, for example 30 to 90 watts, in a cylindrical tabletop device. A cylindrical design is chosen for ease of construction and symmetry with the beverage containers. The cylindrical chamber is somewhat larger than a three liter beverage container and the electronic control circuit is in a separate unit. The cylindrical design is usually avoided for ultrasonic tanks because of poor geometry for ultrasonic waves distribution as compared with more conventional rectangular geometries. The focusing effect of the ultrasonic waves causes interferences similar to those that occur with cylindrical lenses using optical waves. The focusing effect causes more of the ultrasonic energy to be concentrated at the center of the tank which is also the center of the test beverage container and is considered advantageous in this embodiment. However, the control feedback circuit is designed to properly balance the interference problem. More control is achieved with two transducers since each can be generating different frequencies and amplitudes, and the mounting geometry is non-concentric.

A drain can be been provided to control the water level in the ultrasonic tank. This level will vary with container size and evaporation over time. However, as a result of the electronic control circuit, the water level has minimum influence on the ultrasonic power generation except at very low levels. The water interface between the ultrasonic transducer, which is attached to the ultrasonic tank, provides a uniform medium so that the ultrasonic power, amplitude of wave at a particular frequency, is uniformly transmitted to the beverage and can be properly controlled.

One of the problems, especially with beverage cans that have very small head spaces, is getting enough gas to be tested. This is particularly true in the case of oxygen. An expansion chamber, which is normally used for faster testing and most often uses a piston as the expansion element, can slowly be enlarged by drawing the piston away from the sealed container and, thus, effectively increasing the head space of the container. If a pathway is provided to a piston through a valve, pressure in the drink will move the piston back providing an expanded container for the liquid. Much of the beverage in the container is drawn into the piston leaving an expanded head space in the beverage container. Additionally, if the container is agitated, for example by using precision ultrasonics the pressure will be greater because gas will be released into the newly opened space in the container and the movement of the piston will be increased. The expansion chamber, when collapsed by moving the piston forward, drives the gas to be measured in the gas state into the test chamber. As total agitation energy is a function of agitation power and time, precision ultrasonics will accurately control the movement of the piston.

Tests are usually conducted in the test chamber with one or several sensors. For example, sensors to measure $CO_2$, such as an infrared specific sensor, a Severinghaus pH-type sensor or sensors to measure $O_2$, such as a Clark cell, a zirconium oxide cell or an optical cell, are present in the test chamber. Also, more than one sensor, of the same type may be used to insure reliability of the measurement. Although, one purpose of the present invention is to measure the gas in the test chamber, a sensor properly placed in the expansion chamber such as a thermometer or a pH probe would allow certain tests to be performed in that chamber.

Figure 1:
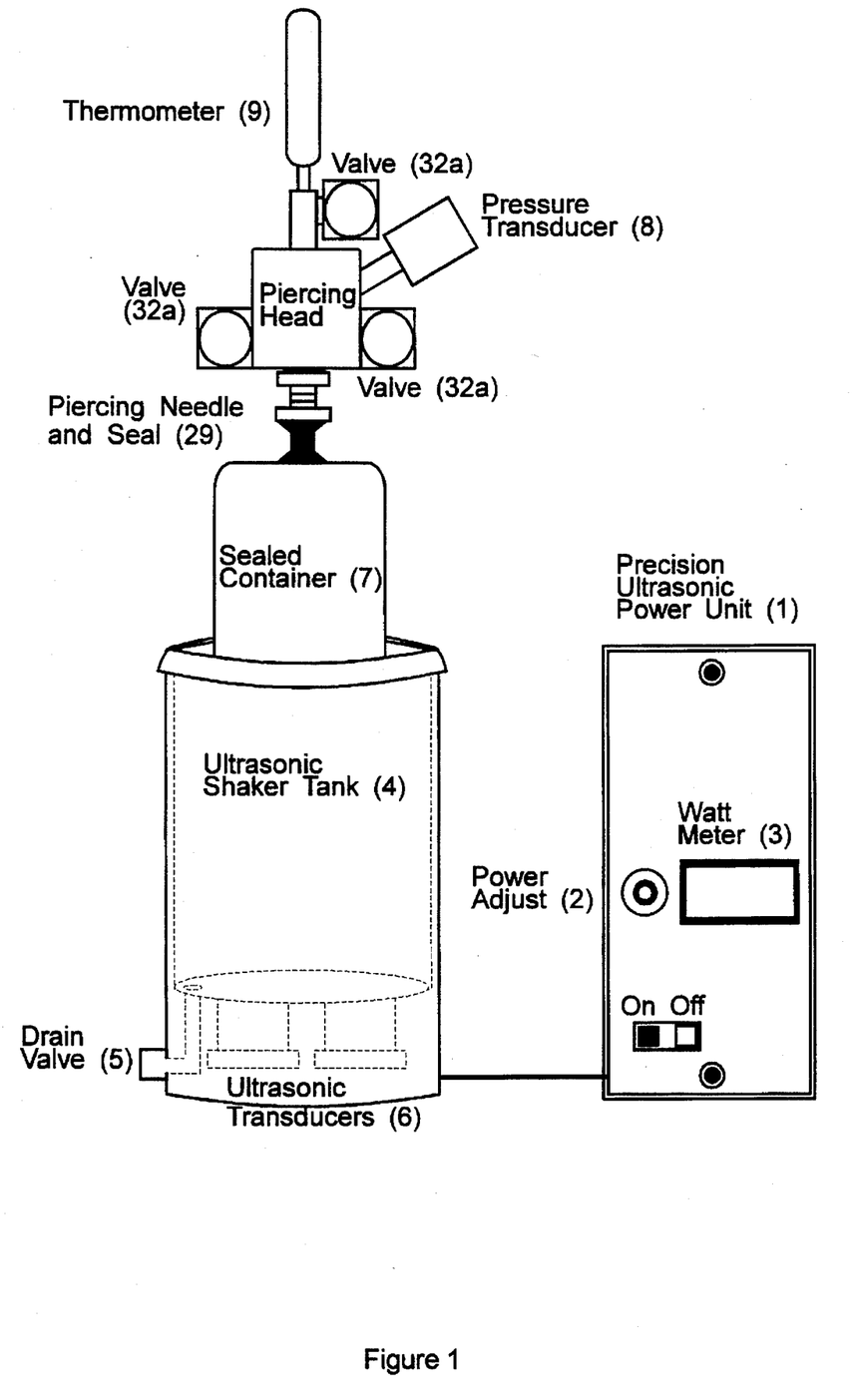
FIG. 1. A precision ultrasonic shaker combined with a non-specific pressure/temperature measurement for determining the $CO_2$ content of beverages.

One embodiment of the present invention comprises three parts: (i) a process for producing controlled agitating power based upon ultrasonics, (ii) an expansion chamber that allows the head space of the beverage to be enlarged, and (iii) degassing techniques such as sparging to be used with non-carbonated liquids that contain organic material. In FIG. 1, the electronic feedback control circuit is contained in the ultrasonic power supply (1). The resistance that determines the power level of the ultrasonics resonance circuit is manually adjusted with the power adjust control (2) and the level of the controlled power through the load is displayed on the watt meter (3). The ultrasonic shaker tank is cylindrical (4) for ease of construction and symmetry with the beverage containers. The load consists of the electronic circuits, the ultrasonic transducer (6), located near the bottom of the ultrasonic shaker tank (4), all the items in the shaker tank, such as the sealed beverage container (7), its supports, and the liquid level in the shaker can. This liquid in the ultrasonic tank (4) connects the ultrasonic transducer (6) transmitted energy to the liquid in the sealed container (7). A drain (5) is located near the ultrasonic transducer to regulate the liquid level in the shaker tank.

Figure 6:
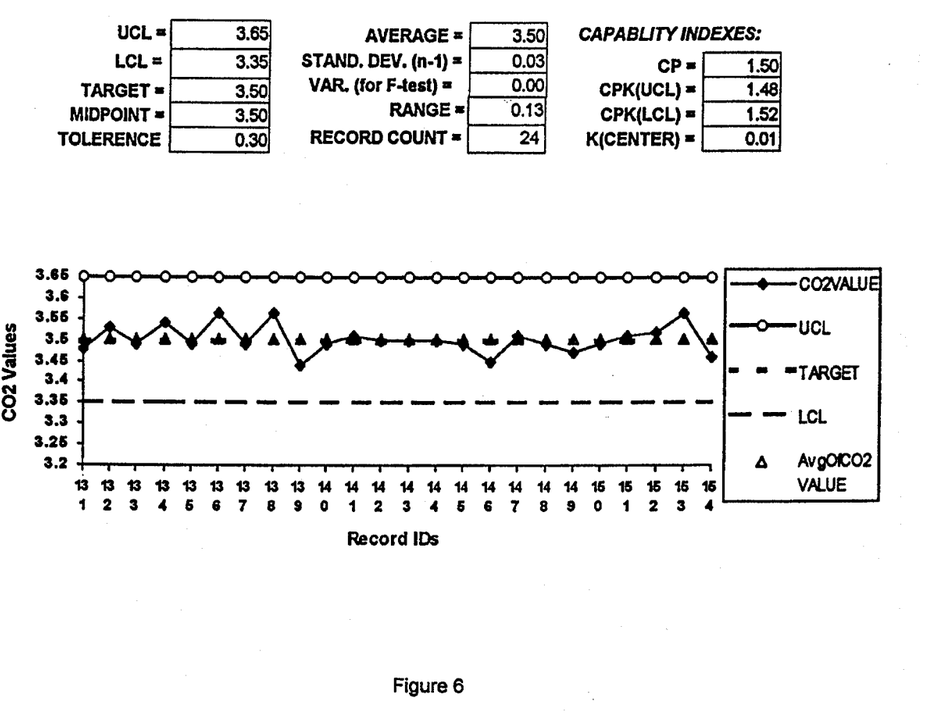
FIG. 6. Graph and statistics for precision ultrasonic characteristics from production beverage containers for $CO_2$ values.

Degassing for $CO_2$ testing, for example, in the non-specific pressure, temperature technique, using for example a pressure transducer (8) and a thermometer (9), for calculating $CO_2$ volumes or another single gas such as $N_2$, is controlled by the power of the precision ultrasonic degassing device. This precision allows the agitation to be limited to a short, controlled degassing, as compared to saturation degassing, without losing the accuracy of the measurement. In addition, even if the test is allowed to go to saturation, the point where the volumes of gas in the head space is in equilibrium with the volume of dissolved gas in the beverage, different power levels of agitation power may give different results. Thus, precision ultrasonics uniquely allows repeatability of measurements as demonstrated in FIG. 6.

Figure 2:
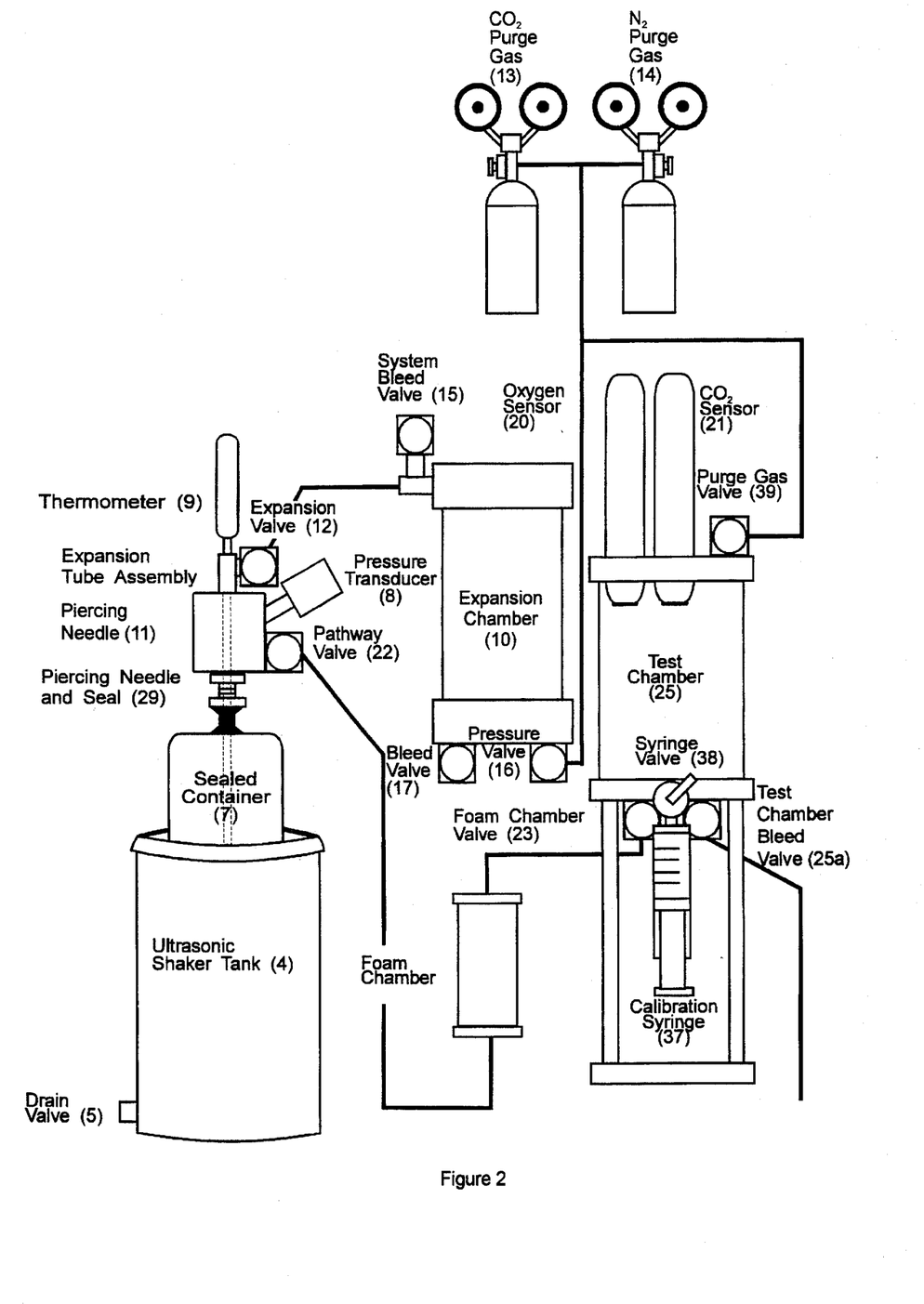
FIG. 2. A precision ultrasonic shaker with an expansion chamber to increase head space in a beverage container and a test chamber for determining the specific $O_2$ and specific $CO_2$ content of the drink.
Figure 3:
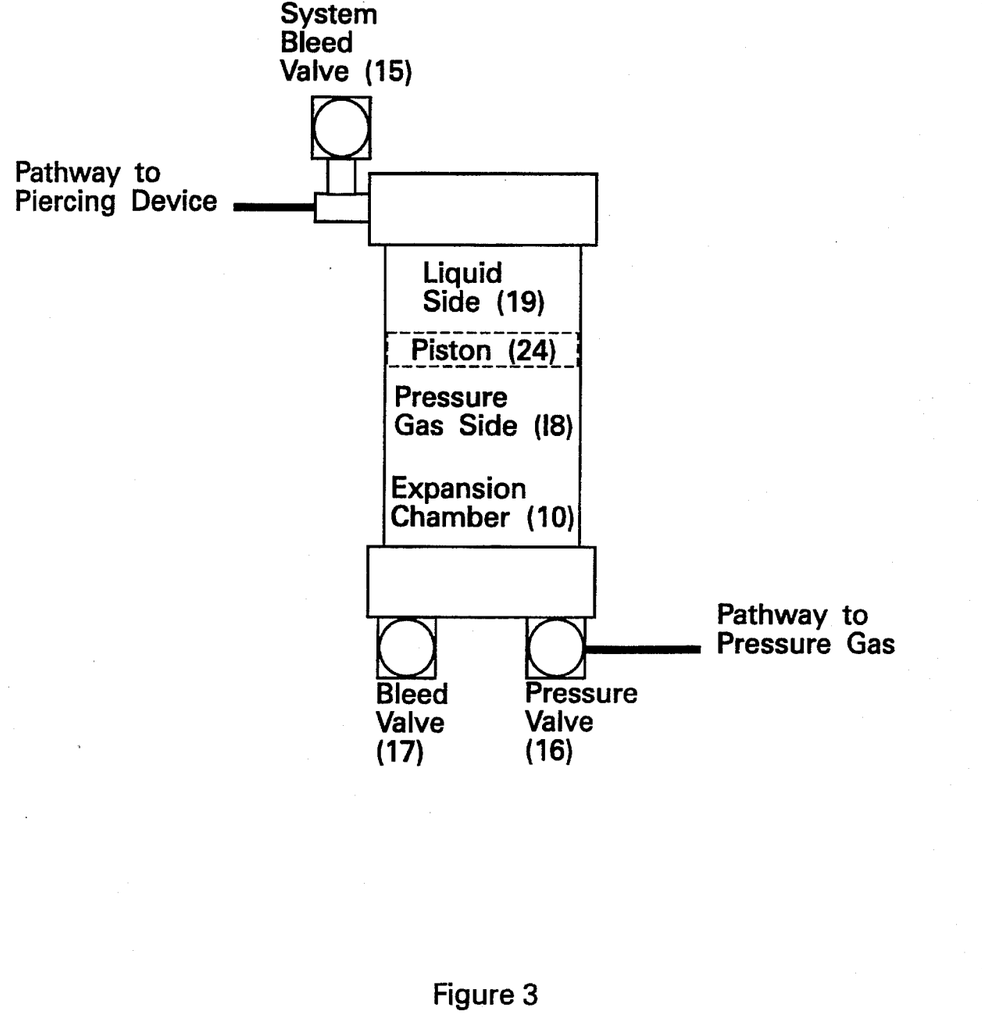
FIG. 3. An enlarged diagram of an expansion chamber designed to contain liquid from a beverage container while enlarging the head space of the beverage container.

One embodiment of the invention is shown in FIGS. 2 and 3. In this embodiment, the expansion chamber (10) is connected to the piercing head (11) through an expansion valve (12). The expansion chamber (10) is also shown in more detail. The minimum position of the piston occurs when it sits at the top of the expansion chamber and the maximum position occurs when it sits at the bottom. The system bleed valve (15) allows gas pressure above the piston to be released when the pressure gas valve (16) is open as seen in FIG. 2. The pressure gas source may be a purge gas container (13a), which is controlled by a gas regulator (13b) such as $CO_2$ (13), $N_2$ (14), or a gas source external to the system such as compressed air. The purged gas valve (39) mounted atop the test chamber allows the purged gas to enter the test chamber. The bleed valve (17) shown in FIGS. 2 and 3 allows the pressure on the pressure gas side (18) of the piston to be minimized. When the expansion valve (12) is open and the system bleed valve (15) is closed, the liquid side (19) of the piston will fill until an equilibrium position is established. The head space in the sealed container will be expanded by the volume of liquid that enters the expansion chamber from the beverage container. The volume is increased with agitation and controlled with precision agitation.

The piston or other expansion element can be moved by external means, such as by gas pressure or a motor. In the return stroke, the piston is moved forward to drive the liquid back into the can as the expansion valve (12) is opened. Also, the pathway valve (22) and the foam chamber valve (23) are opened to the test chamber. This forward motion of the piston (24) allows much more of the gas in the enlarged head space to be pushed into the test chamber (25) in each test cycle. Hence the test is performed much faster since more of the gas is recovered in fewer cycles. Pressurized gas is removed from the test chamber through the test chamber bleed valve (25a).

The test chamber contains one or more sensors (20) (21). These sensors may be specific sensors for measuring $O_2$ and $CO_2$ or non-specific sensors such as thermometers and pressure transducers. Also, there may be more than one sensor of the same type to insure reliability of the measurement. In the case of non-carbonated or lightly carbonated liquids, sparging of the liquid using a gas (26) is generally used to degas the liquid. This process can often be enhanced by cavitation using ultrasonics (27), for example, as shown in FIGS. 4 and 5.

Figure 4:
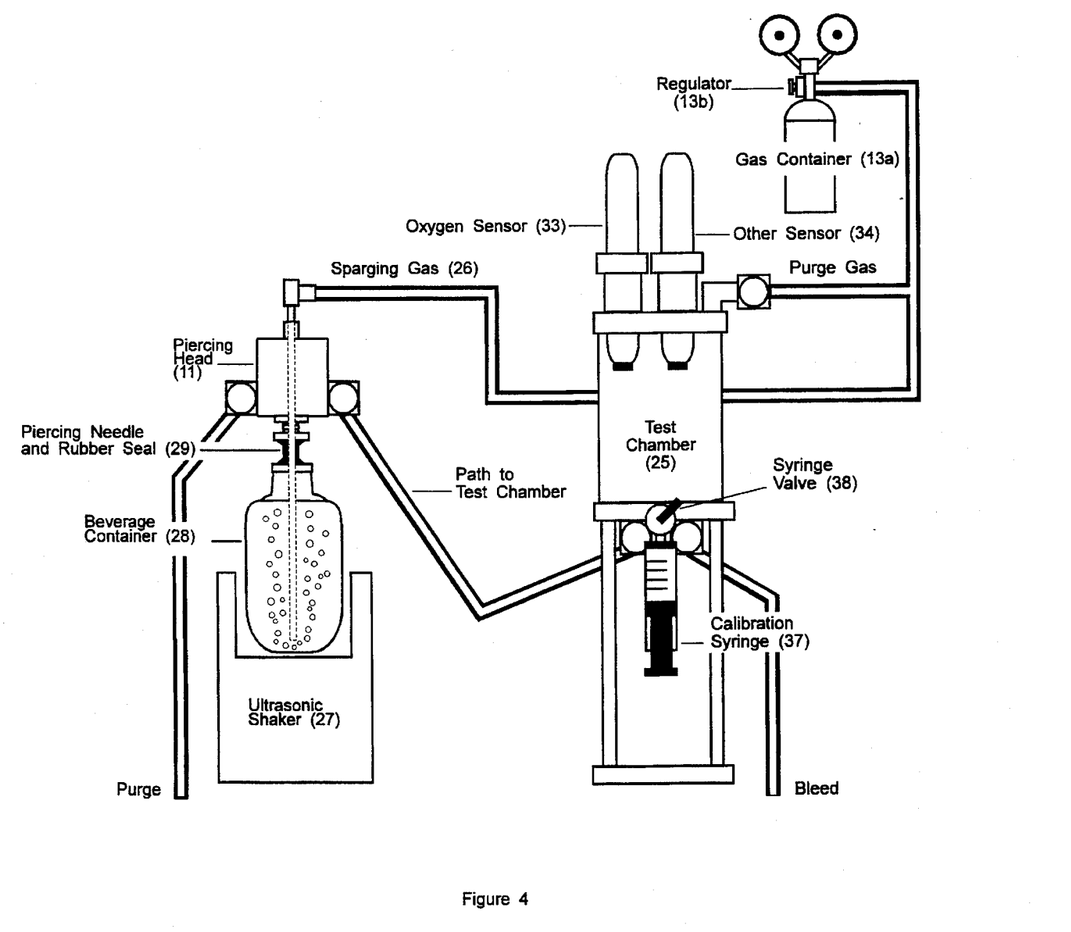
FIG. 4. Combination of sparging with a purge gas and cavitation with ultrasonics for enhanced degassing in a beverage.
Figure 5:
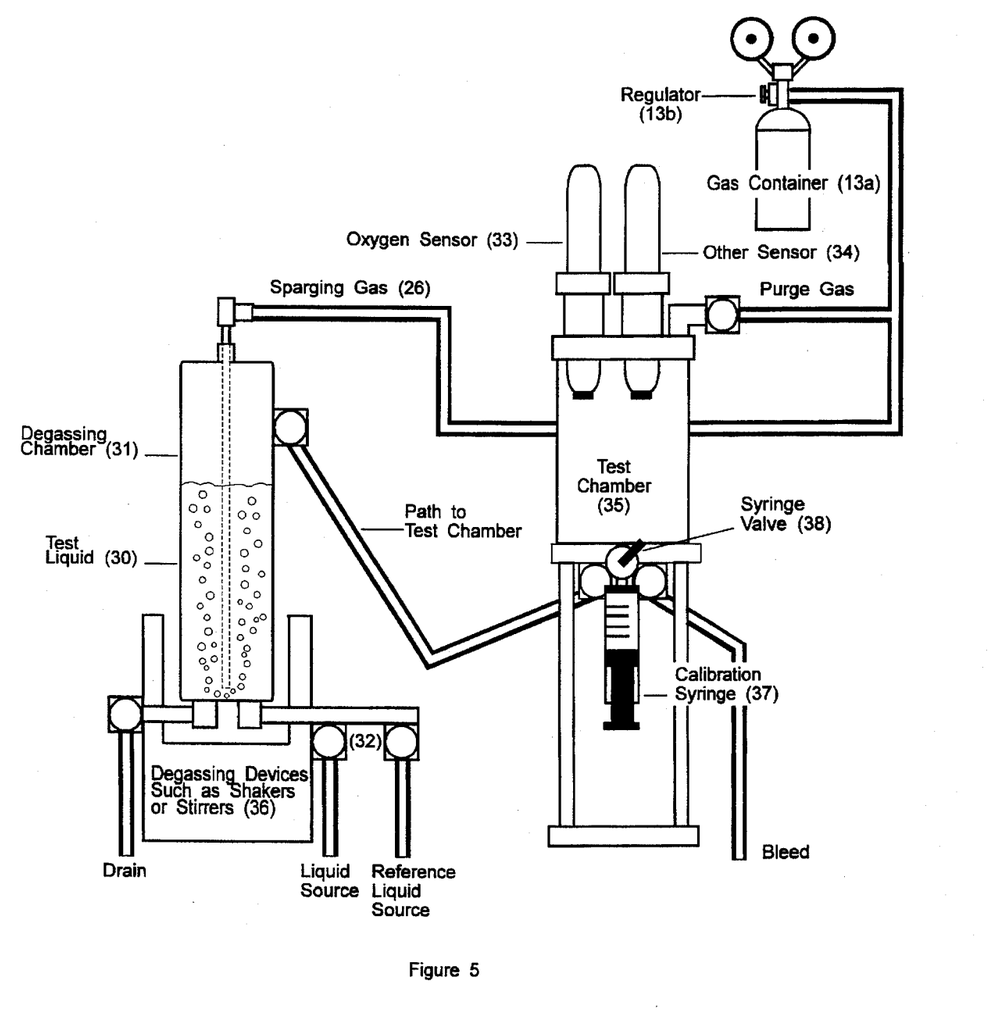
FIG. 5. Combination of sparging with a purge gas and ultrasonics for enhanced degassing of test liquids which may be environmentally difficult liquids such as waste water and activated sludge.

In FIG. 4, the liquid is a beverage in a sealed container (28) and the container is pierced by a piercing needle and then sealed (29). Multiple valves are connected to the piercing head. (32a) In FIG. 5, the test liquid (30) is an imported liquid brought into a degassing chamber (31)

through a set of valves (32) which may allow either test liquid or reference liquid into the degassing chamber. The test chamber, which receives the gas from the degassing chamber, normally will contain an oxygen sensor (33) or another sensor (34), such as a specific gas sensor, temperature sensors, humidity sensors, and pressure sensors. The test chamber is a fixed volume chamber where the natural gas laws may be applied. In FIG. 5, the test chamber (35) may be considered part of a gas only respirometer where the oxygen of interest is measured at various time intervals, for example 10 minutes to several hours, and receives the released gas from a collected test liquid (30). The test liquid is degassed in the degassing chamber (31). Normally this could be done with a sparging gas. Other degassing techniques may also be useful in assisting this process from the group of degassing devices (36) such as ultrasonics, magnetic stirrers, mechanical devices and vacuum techniques.

The degassing of lightly carbonated liquids can be enhanced by a combination of sparging and ultrasonic cavitation. Sparging is defined as the bubbling or sprinkling of a gas through the liquid to accelerate the degassing process to remove a specific gas component or components from the liquid. Cavitation is defined as the rapid formation and collapse of vapor pockets or bubbles in a liquid in regions of very low pressures; this effect is most pronounced when the bubbles in the liquid interact with ultrasonic waves. For example, $N_2$ is the sparging gas and $O_2$ is the gas to be removed from the liquid. The sparging gas and the purging gas (the gas used to remove a specific gas such as extraneous $O_2$ from the system before starting a new test), are generally, but not necessarily the same gas. The combination action, introducing bubbles into the liquid (sparging) and energizing those bubbles with ultrasonics (cavitation), allows for a controlled and optimized degassing process often more efficient than either process alone, since the cavitation enhances the energy and activity of the introduced bubbles.

In addition, this same process can be adapted to measure specific gases, especially oxygen, in many other types of liquid besides beverages, including liquids that have important environmental considerations and contain organic materials. In many cases, it is often not desirable to have the test sensor in the liquid since the sensor is frequently fouled and difficult to calibrate. In a production process, the maintenance of the sensor and the ease of calibration, as allowed in the gas test chamber, are important.

The oldest measure of metabolism in a liquid is the conventional biological or biochemical oxygen demand test (BOD). Many facilities do not have the time or storage space to wait the 5 days necessary for conventional testing and are looking for practical and legislative relief. Therefore, short term oxygen demand tests (STOD) are now used whenever possible. The combination of cavitation and sparging permits quicker analysis of certain oxygen consuming properties of the test liquid. These short term measurements, STOD and SBOD, involve rate of change or first derivative considerations often referred to as oxygen uptake as a function of time. Sparging is the principle degassing technique for removing oxygen from a liquid that is non-carbonated. The measurements are made in a test chamber containing the gas that has been removed from the degassed liquid.

A respiration cell was developed using an oxygen probe in the liquid to study the responses of industrial wastes to biological treatment (Mancy and Westgarth, *Water and Water Pollution Handbook* Vol. 4:1476, 1973). Also, respiration rates have been studied by Spanjers, Olsson, and Klapwijk (Wat. Res. Vol. 28(7):1571–83, 1994). In this case, the measuring oxygen sensor is also placed in the liquid. In this invention, respiration, the rate of consumption of the oxygen by bacteria, is measured outside of the liquid in a sealable gas test chamber after the liquid has been degassed. A reference liquid can be introduced into a liquid chamber that has a low oxygen consumption rate. This may be endogenous sludge or a degassed liquid. Endogenous sludge is a liquid with no organic carbon source available to the bacteria but may contain other suspended solids.

In such cases, another degassing technique which can be used is sparging. Sparging involves bubbling one or more gasses into a liquid to remove other dissolved gasses. It is the primary degassing technique for liquids in sealed or closed containers that are non-carbonated or lightly carbonated. A third degassing technique which may be useful is stirring, such as magnetic stirring. This is described in U.S. Pat. Nos. 4,607,342 and 5,220,513 (hereby specifically incorporated by reference). Sparging can be used for degassing both carbonated and non-carbonated liquids. The three degassing techniques can be used to release dissolved oxygen from a liquid so that the gas may enter a test chamber for measurement. They may be used either alone or in combination, depending on the characteristics of the sample to be degassed and the geometry of the container, for a number of processes including determination of the oxygen content of beverages, edible oils and waste liquids such as waste water and activated sludge.

Sparging can be used to degas waste water and activated sludge when the respiration rate of bacteria is to be measured in a fixed volume test chamber. The activated sludge process is a biological waste water treatment technique in which a mixture of waste water and biological sludge containing microorganisms is agitated and aerated.

The fixed volume test chamber can be used to measure the respiration rate of bacteria in waste water or activated sludge. For example, waste water flows continuously into an aeration tank where air is injected to mix activated sludge with waste water and supply the oxygen needed for the organisms to break down the organics. By periodically degassing a portion of this aerated mixture, which is sometimes referred to as a mixed liquor, and periodically measuring the respiration gasses, which is usually oxygen, the respiration rate of the bacteria which changes as a function of the aeration process and the organics available to the bacteria can be determined. This respiration rate can be used to directly determine short term BOD (SBOD) which can be projected to give long term BOD results when the mixture under test is reasonably constant (*A Short Term Biological Oxygen Demand Test* Verimmen, Henken and Lamb, Vol. 39(6):1006, J. WPCS).

The measurement, which represents the status of oxygen consumed in the liquid, may be an integration over time or a series of discrete measurements. The reference liquid may be an oxygen stable or endogenous sample or a degassed liquid using sparging and ultrasonic techniques. Table 1 shows the relationship between oxygen in a test chamber after degassing and the dissolved oxygen in a liquid before degassing. In this case, the test chamber that receives released oxygen is about 400 cc. Oxygen may be introduced as a gas for calibration, for example as a 1 cc injection of air (Table 1, row 8, column A), which is injected into the oxygen-free test chamber or from a degassed liquid (Table 1, row 3, column E). The final result can be normalized to milligrams per liter.

The following experiments are offered to illustrate embodiments of the invention, and should not be viewed as limiting the scope of the invention.

EXAMPLES

Example 1 Speed.

Highly accurate and repeatable oxygen measurements are required in beverage packaging since low levels of oxygen can cause product and/or container degradation. However, testing speed is also important in order to minimize the volume of off-specification product manufactured and therefore discarded. By incorporating the expansion chamber into the air testing system, the number of measurements required may be decreased from five to two. The measurement process can be completed 60% faster when this technique is used.

Example 2 Comparison Testing.

Many beverage packagers send products to a central laboratory for comparison testing. Also, some parent companies take product off the retail shelf and test them. While the typical ultrasonic shaker will provide internally consistent results under the same conditions (input electric current, water level, etc.), over time the unit's power output may change. Moreover, if the central laboratory obtains different test results for whatever reason, there is no way to match the testing procedure since the typical ultrasonic shaker cannot be adjusted.

Precision ultrasonics eliminates these problems. The unit has a power output watt meter, thus, the shaking output is always known. If there is a change in the shaking power, the unit can be adjusted. Moreover, if there is a difference in test results between the central laboratory and the beverage packager, the unit can be adjusted to match the shaking power used in the central laboratory. Often discrepancies are traced to the agitation process. Precision ultrasonics eliminates this process as a variable in the final result.

Example 3

Experimental Data.

Twenty-four carbonated samples (beverage cans) were pulled from a production line and test for $CO_2$ using precision ultrasonics. Each sample can was filled at the same filler head to eliminate "fill" as much as possible as a variable. Since temperature and pressure are also variables and the $CO_2$ values shown in FIG. 6 a function of both of those parameters and a look up table that is not perfect, it is reasonable to say that precision ultrasonics completely eliminates variation in cavitation energy as a variable. This is the major objection to ultrasonic degassing, sometimes also referred to as ultrasonic shaking or agitation. Note in FIG. 6 the graphical representation of the data. The statistical average is very close to the target and the standard deviation is very small.

Example 4 Comparison Of Dissolved Oxygen v. Oxygen Removed by Degassing.

Often it is difficult to compare dissolved oxygen in a liquid to the oxygen in a fixed volume test chamber after it is removed from the container by degassing. Experiments were performed to relate the amounts of oxygen in a test gas chamber to the amount of dissolved oxygen in a liquid.

TABLE 1

Oxygen Calculations of Test Chamber v. Liquid Container

| | Closed 400 cc Test Chamber Containing $O_2$ as a Gas | | | | Distilled Water (STP) Containing Dissolved Oxygen | |
|---|---|---|---|---|---|---|
| A Sample | B Air (cc) | C $O_2$ (cc) | D % $O_2$ | E $O_2$ (mg) | F $O_2$ (mg) | G mg/l $O_2$ |
| 1 | 400(c) | 80.0 | 21.(b) | 112.0 | 112(e) | 9.0(a) |
| 2 | 50.0 | 10.0 | 2.6 | 14.0 | 14.0 | 1.1 |
| 3 | 44.5 | 8.9 | 2.3 | 12.4 | 12.4 | 1.0(e) |
| 4 | 19.0 | 3.8 | 1.0 | 5.3 | 5.3 | 0.43 |
| 5 | 10.0 | 2.0 | 0.53 | 2.8 | 2.8 | 0.23 |
| 6 | 5.0 | 1.0 | 0.26 | 1.4 | 1.4 | 0.11 |
| 7 | 1.9 | 0.38 | 0.1 | 0.53 | 0.53 | 0.043 |
| 8 | 1.0(d) | 0.2 | 0.053 | 0.28 | 0.28 | 0.023 |
| 9 | 0.5 | 0.1 | 0.026 | 0.14 | 0.14. | 0.011 |
| 10 | 0.45 | 0.09 | 0.023 | 0.123 | 0.123 | 0.01 |
| 11 | 0.05 | 0.01 | 0.0026 | 0.014 | 0.014 | 0.0011 |
| 12 | 0.045 | 0.009 | 0.0023 | 0.0123 | 0.0123 | 0.001 |

(a) Generally considered saturation in distilled water. This column is used when the gas is derived from dissolved gas in a liquid. The gas is piped into the test chamber from the liquid using various degassing techniques. Other liquids would give different numbers.

(b) This sample is at one atmosphere of air which is about 21% oxygen by volume at sea level. 21% (14.7 lbs.) yields about 3.1 lb./in$^2$ partial pressure of oxygen.

(c) The nominal test chamber is about 400 cc filled with one atmosphere of Air. The test chamber can be purged with oxygen-free nitrogen at any time.

(d) Consider an injection of Air (1 cc) pushed with a syringe into the test chamber which contains no oxygen but only pure nitrogen at atmospheric pressure. This syringe is a calibration syringe (37) and is connected to the test chamber through a syringe valve (38). 400 injections would fill the chamber with 3.1 lb./in$^2$ partial pressure of oxygen—see (b). If the chamber is filled by injections rather than opened to the atmosphere—see (c)—the amount of $N_2$ partial pressure would be approximately doubled.

(e) Consider that the oxygen was dissolved in distilled water (in this case 1 mg of oxygen) and the liquid was degassed. The gas is piped into the test chamber. The multiplier to get 12.4 mg in the closed chamber of 400 cc is 12.4. In other words, 12.4 liters of liquid with the indicated concentration of oxygen would have to be degassed to get an equivalent amount of oxygen in the test chamber.

Other embodiments and uses of the invention will be apparent to those skilled in the art from consideration of the specification and practice of the invention disclosed herein. The specification and examples should be considered exemplary only with the true scope and spirit of the invention indicated by the following claims.

We claim:

1. A method for measuring the respiration rate of bacteria comprising the steps of:
   a) filling a degassing chamber with a test liquid containing bacteria;
   b) degassing the chamber;
   c) receiving a sample of a gas released from the degassing chamber into a test chamber and optionally passing the sample through at least one additional chamber;
   d) measuring an amount of a component of said gas of said sample in the test chamber with a gas specific sensor; and
   e) determining the respiration rate of bacteria of the liquid.

2. The method of claim 1 wherein the test liquid is activated waste water or activated sludge.

3. The method of claim 1 wherein the test chamber contains the sensors for measuring the gases released from the respiration chamber.

4. The method of claim 1 wherein the degassing step is performed by sparging or stirring.

5. The method of claim 1 wherein the one additional chamber is an expansion chamber, a buffer chamber or an extra test chamber.

6. The method of claim 4 wherein sparging is assisted by another degassing technique comprised of stirring or shaking.

* * * * *